United States Patent
Ross et al.

(10) Patent No.: US 9,649,149 B2
(45) Date of Patent: *May 16, 2017

(54) RF GENERATOR SYSTEM FOR SURGICAL VESSEL SEALING

(71) Applicant: Just Right Surgical, LLC, Louisville, CO (US)

(72) Inventors: David Ross, Orange, CT (US); Joel Helfer, Cheshire, CT (US)

(73) Assignee: JUST RIGHT SURGICAL, LLC, Louisville, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 14/704,587

(22) Filed: May 5, 2015

(65) Prior Publication Data

US 2015/0230854 A1    Aug. 20, 2015

Related U.S. Application Data

(63) Continuation of application No. 13/277,979, filed on Oct. 20, 2011, now Pat. No. 9,039,694.

(Continued)

(51) Int. Cl.
*A61B 18/12* (2006.01)
*H02M 7/539* (2006.01)
(Continued)

(52) U.S. Cl.
CPC ........ *A61B 18/1233* (2013.01); *H02M 7/539* (2013.01); *A61B 18/1442* (2013.01);
(Continued)

(58) Field of Classification Search
CPC ............... A61B 18/12; A61B 18/1206; A61B 2018/00702
(Continued)

(56) References Cited

U.S. PATENT DOCUMENTS 4,569,345 A    2/1986    Manes
4,574,801 A    3/1986    Manes
(Continued)

FOREIGN PATENT DOCUMENTS

JP    61222441         2/1986
JP    61222441 A    10/1986
(Continued)

OTHER PUBLICATIONS

Yagi, Keita, "Japanese Office Action re Application No. 2013-535106", Aug. 18, 2015, p. 6 Published in: JP.

(Continued)

*Primary Examiner* — Allen Porter, Jr.
(74) *Attorney, Agent, or Firm* — Neugeboren O'Dowd PC

(57) ABSTRACT

Systems, methods, and apparatus for providing power to an electrosurgical instrument. A method of providing power to an electrosurgical instrument includes generating a non-sinusoidal driving voltage having a substantially constant driving frequency; providing the non-sinusoidal driving voltage to a series LC circuit having a resonant frequency of substantially twice the substantially constant driving frequency and configured to present an impedance that limits current spikes and voltage transient spikes during load fluctuations; generating a quasi-sinusoidal current in the series LC circuit from the non-sinusoidal driving voltage; and providing the quasi-sinusoidal current to an electrical output, wherein the electrical output is configured for coupling to an electrical input of a bipolar tissue-sealing surgical instrument.

19 Claims, 7 Drawing Sheets

Related U.S. Application Data

(60) Provisional application No. 61/405,761, filed on Oct. 22, 2010.

(51) Int. Cl.
*A61B 18/14* (2006.01)
*A61B 18/00* (2006.01)

(52) U.S. Cl.
CPC ............... *A61B 2018/0063* (2013.01); *A61B 2018/00702* (2013.01); *A61B 2018/00779* (2013.01); *A61B 2018/00827* (2013.01); *A61B 2018/00875* (2013.01); *A61B 2018/00892* (2013.01)

(58) Field of Classification Search
USPC ..................................................... 606/32–42
See application file for complete search history.

(56) References Cited

U.S. PATENT DOCUMENTS

| | | |
|---|---|---|
| 4,617,927 A | 10/1986 | Manes |
| 4,658,819 A | 4/1987 | Harris et al. |
| 4,658,820 A | 4/1987 | Klicek |
| 4,850,353 A | 7/1989 | Stasz et al. |
| 4,903,696 A | 2/1990 | Stasz et al. |
| 4,905,691 A | 3/1990 | Rydell |
| 4,936,281 A | 6/1990 | Stasz |
| 4,961,739 A | 10/1990 | Thompson |
| 5,007,908 A | 4/1991 | Rydell |
| 5,013,312 A | 5/1991 | Parins et al. |
| 5,047,026 A | 9/1991 | Rydell |
| 5,258,006 A | 11/1993 | Rydell et al. |
| 5,282,799 A | 2/1994 | Rydell |
| 5,304,190 A | 4/1994 | Reckelhoff et al. |
| 5,342,359 A | 8/1994 | Rydell |
| 5,342,381 A | 8/1994 | Tidemand |
| 5,352,222 A | 10/1994 | Rydell |
| 5,356,408 A | 10/1994 | Rydell |
| 5,403,312 A | 4/1995 | Yates et al. |
| 5,445,638 A | 8/1995 | Rydell et al. |
| 5,447,513 A | 9/1995 | Davison et al. |
| 5,458,598 A | 10/1995 | Feinberg et al. |
| 5,462,546 A | 10/1995 | Rydell |
| 5,484,435 A | 1/1996 | Fleenor et al. |
| 5,496,317 A | 3/1996 | Goble et al. |
| 5,514,134 A | 5/1996 | Rydell et al. |
| 5,540,684 A | 7/1996 | Hassler, Jr. |
| 5,540,685 A | 7/1996 | Parins et al. |
| 5,571,100 A | 11/1996 | Goble et al. |
| 5,573,424 A | 11/1996 | Poppe |
| 5,599,344 A | 2/1997 | Paterson |
| 5,599,350 A | 2/1997 | Schulze et al. |
| 5,603,711 A | 2/1997 | Parins et al. |
| 5,611,798 A | 3/1997 | Eggers |
| 5,624,452 A | 4/1997 | Yates |
| 5,637,111 A | 6/1997 | Sutcu et al. |
| 5,647,869 A | 7/1997 | Goble et al. |
| 5,666,035 A | 9/1997 | Basire et al. |
| 5,667,480 A | 9/1997 | Knight et al. |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,716,366 A | 2/1998 | Yates |
| 5,722,934 A | 3/1998 | Knight et al. |
| 5,725,479 A | 3/1998 | Knight et al. |
| 5,735,848 A | 4/1998 | Yates et al. |
| 5,735,849 A | 4/1998 | Baden et al. |
| 5,743,906 A | 4/1998 | Parins et al. |
| 5,766,170 A | 6/1998 | Eggers |
| 5,769,849 A | 6/1998 | Eggers |
| 5,776,128 A | 7/1998 | Eggers |
| 5,776,130 A | 7/1998 | Buysse et al. |
| 5,797,938 A | 8/1998 | Paraschac et al. |
| 5,807,392 A | 9/1998 | Eggers |
| 5,807,393 A | 9/1998 | Williamson, IV et al. |
| 5,810,805 A | 9/1998 | Sutcu et al. |
| 5,810,808 A | 9/1998 | Eggers |
| 5,810,811 A | 9/1998 | Yates et al. |
| 5,817,093 A | 10/1998 | Williamson, IV et al. |
| 5,827,271 A | 10/1998 | Buysse et al. |
| 5,833,690 A | 11/1998 | Yates et al. |
| 5,860,975 A | 1/1999 | Goble et al. |
| 5,876,401 A | 3/1999 | Schulze et al. |
| 5,891,141 A | 4/1999 | Rydell |
| 5,891,142 A | 4/1999 | Eggers et al. |
| 5,902,301 A | 5/1999 | Olig |
| 5,908,420 A | 6/1999 | Parins et al. |
| 5,911,719 A | 6/1999 | Eggers |
| 5,921,984 A | 7/1999 | Sutcu et al. |
| 5,928,135 A | 7/1999 | Knight et al. |
| 5,928,138 A | 7/1999 | Knight et al. |
| 6,024,741 A | 2/2000 | Williamson, IV et al. |
| 6,024,744 A | 2/2000 | Kese et al. |
| 6,039,733 A | 3/2000 | Buysse et al. |
| 6,063,086 A | 5/2000 | Benecke et al. |
| RE36,795 E | 7/2000 | Rydell |
| 6,093,186 A | 7/2000 | Goble |
| 6,096,037 A | 8/2000 | Mulier et al. |
| 6,096,058 A | 8/2000 | Boche |
| 6,102,909 A | 8/2000 | Chen et al. |
| 6,110,171 A | 8/2000 | Rydell |
| 6,117,152 A | 9/2000 | Huitema |
| 6,126,675 A | 10/2000 | Shchervinsky et al. |
| 6,165,175 A | 12/2000 | Wampler et al. |
| 6,179,834 B1 | 1/2001 | Buysse et al. |
| 6,187,003 B1 | 2/2001 | Buysse et al. |
| 6,190,386 B1 | 2/2001 | Rydell |
| 6,193,653 B1 | 2/2001 | Evans et al. |
| 6,206,823 B1 | 3/2001 | Kolata et al. |
| 6,206,878 B1 | 3/2001 | Bishop et al. |
| 6,228,080 B1 | 5/2001 | Gines |
| 6,238,387 B1 | 5/2001 | Miller, III |
| 6,277,117 B1 | 8/2001 | Tetzlaff et al. |
| 6,293,945 B1 | 9/2001 | Parins et al. |
| 6,296,640 B1 | 10/2001 | Wampler et al. |
| 6,352,536 B1 | 3/2002 | Buysse et al. |
| 6,358,249 B1 | 3/2002 | Chen et al. |
| 6,361,534 B1 | 3/2002 | Chen et al. |
| 6,364,879 B1 | 4/2002 | Chen et al. |
| 6,398,779 B1 | 6/2002 | Buysse et al. |
| 6,419,675 B1 | 7/2002 | Gallo, Sr. |
| 6,436,096 B1 | 8/2002 | Hareyama |
| 6,440,130 B1 | 8/2002 | Mulier et al. |
| 6,443,952 B1 | 9/2002 | Mulier et al. |
| 6,443,970 B1 | 9/2002 | Schulze et al. |
| 6,458,128 B1 | 10/2002 | Schulze |
| 6,458,130 B1 | 10/2002 | Frazier et al. |
| 6,464,702 B2 | 10/2002 | Schulze et al. |
| 6,468,275 B1 | 10/2002 | Wampler et al. |
| 6,485,490 B2 | 11/2002 | Wampler et al. |
| 6,511,476 B2 | 1/2003 | Hareyama |
| 6,511,480 B1 | 1/2003 | Tetzlaff et al. |
| 6,527,771 B1 | 3/2003 | Weadock et al. |
| 6,547,786 B1 | 4/2003 | Goble |
| 6,554,829 B2 | 4/2003 | Schulze et al. |
| 6,572,615 B2 | 6/2003 | Schulze et al. |
| 6,582,427 B1 | 6/2003 | Goble et al. |
| 6,585,735 B1 | 7/2003 | Frazier et al. |
| 6,592,582 B2 | 7/2003 | Hess et al. |
| 6,592,604 B2 | 7/2003 | Hess et al. |
| 6,607,529 B1 | 8/2003 | Jones et al. |
| 6,610,060 B2 | 8/2003 | Mulier et al. |
| 6,613,048 B2 | 9/2003 | Mulier et al. |
| 6,616,656 B2 | 9/2003 | Brommersma |
| 6,616,662 B2 | 9/2003 | Scholer et al. |
| 6,620,161 B2 | 9/2003 | Schulze et al. |
| 6,623,482 B2 | 9/2003 | Pendekanti et al. |
| 6,652,521 B2 | 11/2003 | Schulze |
| 6,656,176 B2 | 12/2003 | Hess et al. |
| 6,667,685 B2 | 12/2003 | Wasaki et al. |
| 6,679,892 B2 | 1/2004 | Guido et al. |
| 6,682,528 B2 | 1/2004 | Frazier et al. |

(56) References Cited

U.S. PATENT DOCUMENTS

| | | |
|---|---|---|
| 6,695,840 B2 | 2/2004 | Schulze |
| 6,726,686 B2 | 4/2004 | Buysse et al. |
| 6,736,813 B2 | 5/2004 | Yamauchi et al. |
| 6,740,102 B2 | 5/2004 | Hess et al. |
| 6,743,229 B2 | 6/2004 | Buysse et al. |
| 6,755,827 B2 | 6/2004 | Mulier et al. |
| 6,770,072 B1 | 8/2004 | Truckai et al. |
| 6,773,409 B2 | 8/2004 | Truckai et al. |
| 6,773,435 B2 | 8/2004 | Schulze et al. |
| 6,776,780 B2 | 8/2004 | Mulier et al. |
| 6,790,217 B2 | 9/2004 | Schulze et al. |
| 6,796,981 B2 | 9/2004 | Wham et al. |
| 6,832,998 B2 | 12/2004 | Goble |
| 6,835,195 B2 | 12/2004 | Schulze et al. |
| 6,843,789 B2 | 1/2005 | Goble |
| 6,855,142 B2 | 2/2005 | Harano et al. |
| 6,887,240 B1 | 5/2005 | Lands et al. |
| 6,905,497 B2 | 6/2005 | Truckai et al. |
| 6,926,716 B2 | 8/2005 | Baker et al. |
| 6,929,641 B2 | 8/2005 | Goble et al. |
| 6,929,644 B2 | 8/2005 | Truckai et al. |
| 6,942,662 B2 | 9/2005 | Goble et al. |
| 6,960,209 B2 | 11/2005 | Clague et al. |
| 6,966,907 B2 | 11/2005 | Goble |
| 6,966,909 B2 | 11/2005 | Marshall et al. |
| 7,001,382 B2 | 2/2006 | Gallo, Sr. |
| 7,011,657 B2 | 3/2006 | Truckai et al. |
| 7,033,356 B2 | 4/2006 | Latterell et al. |
| 7,041,102 B2 | 5/2006 | Truckai et al. |
| 7,063,699 B2 | 6/2006 | Hess et al. |
| 7,070,597 B2 | 7/2006 | Truckai et al. |
| 7,083,619 B2 | 8/2006 | Truckai et al. |
| 7,087,054 B2 | 8/2006 | Truckai et al. |
| 7,112,201 B2 | 9/2006 | Truckai et al. |
| 7,118,570 B2 | 10/2006 | Tetzlaff et al. |
| 7,125,409 B2 | 10/2006 | Truckai et al. |
| 7,131,970 B2 | 11/2006 | Moses et al. |
| 7,137,980 B2 | 11/2006 | Buysse et al. |
| 7,147,637 B2 | 12/2006 | Goble |
| 7,150,748 B2 | 12/2006 | Ebbutt et al. |
| 7,153,300 B2 | 12/2006 | Goble |
| 7,169,146 B2 | 1/2007 | Truckai et al. |
| 7,179,258 B2 | 2/2007 | Buysse et al. |
| 7,186,253 B2 | 3/2007 | Truckai et al. |
| 7,189,231 B2 | 3/2007 | Clague et al. |
| 7,189,233 B2 | 3/2007 | Truckai et al. |
| 7,204,835 B2 | 4/2007 | Latterell et al. |
| 7,211,084 B2 | 5/2007 | Goble et al. |
| 7,214,224 B2 | 5/2007 | Goble |
| 7,220,260 B2 | 5/2007 | Fleming et al. |
| 7,241,296 B2 | 7/2007 | Buysse et al. |
| 7,255,696 B2 | 8/2007 | Goble et al. |
| 7,261,724 B2 | 8/2007 | Molitor et al. |
| 7,267,677 B2 | 9/2007 | Johnson et al. |
| 7,288,098 B2 | 10/2007 | Huitema et al. |
| 7,297,149 B2 | 11/2007 | Vitali et al. |
| 7,303,557 B2 | 12/2007 | Wham et al. |
| 7,311,709 B2 | 12/2007 | Truckai et al. |
| 7,322,975 B2 | 1/2008 | Goble et al. |
| 7,329,256 B2 | 2/2008 | Johnson et al. |
| 7,354,440 B2 | 4/2008 | Truckai et al. |
| 7,364,577 B2 | 4/2008 | Wham et al. |
| 7,381,209 B2 | 6/2008 | Truckai et al. |
| 7,491,199 B2 | 2/2009 | Goble |
| 7,510,556 B2 | 3/2009 | Nguyen et al. |
| 7,513,898 B2 | 4/2009 | Johnson et al. |
| 7,553,312 B2 | 6/2009 | Tetzlaff et al. |
| 7,582,087 B2 | 9/2009 | Tetzlaff et al. |
| 7,632,269 B2 | 12/2009 | Truckai et al. |
| 7,648,499 B2 | 1/2010 | Orszulak et al. |
| 7,717,910 B2 | 5/2010 | Goble |
| 7,722,602 B2 | 5/2010 | Mihori |
| 2003/0014053 A1 | 1/2003 | Nguyen et al. |
| 2003/0073987 A1 | 4/2003 | Sakurai et al. |
| 2003/0109875 A1 | 6/2003 | Tetzlaff et al. |
| 2003/0114874 A1 | 6/2003 | Craig et al. |
| 2003/0139741 A1 | 7/2003 | Goble et al. |
| 2003/0181910 A1 | 9/2003 | Dycus et al. |
| 2003/0195544 A1 | 10/2003 | Hess et al. |
| 2004/0006340 A1 | 1/2004 | Latterell et al. |
| 2004/0097921 A1 | 5/2004 | Hess et al. |
| 2004/0122423 A1 | 6/2004 | Dycus et al. |
| 2004/0143263 A1 | 7/2004 | Schechter et al. |
| 2004/0186492 A1 | 9/2004 | Hess et al. |
| 2004/0249374 A1 | 12/2004 | Tetzlaff et al. |
| 2005/0101945 A1 | 5/2005 | Sakurai et al. |
| 2005/0101952 A1 | 5/2005 | Lands et al. |
| 2005/0134324 A1 | 6/2005 | Boyer et al. |
| 2005/0203504 A1 | 9/2005 | Wham et al. |
| 2005/0203507 A1 | 9/2005 | Truckai et al. |
| 2005/0261676 A1 | 11/2005 | Hall et al. |
| 2005/0261677 A1 | 11/2005 | Hall et al. |
| 2005/0267464 A1 | 12/2005 | Truckai et al. |
| 2006/0030848 A1 | 2/2006 | Craig et al. |
| 2006/0047275 A1 | 3/2006 | Goble |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0235468 A1 | 10/2006 | Huitema et al. |
| 2006/0259036 A1 | 11/2006 | Tetzlaff et al. |
| 2006/0264929 A1 | 11/2006 | Goble et al. |
| 2006/0271042 A1 | 11/2006 | Latterell et al. |
| 2007/0016235 A1 | 1/2007 | Tanaka et al. |
| 2007/0038209 A1 | 2/2007 | Buysse et al. |
| 2007/0062017 A1 | 3/2007 | Dycus et al. |
| 2007/0118163 A1 | 5/2007 | Boudreaux et al. |
| 2007/0146113 A1 | 6/2007 | Truckai et al. |
| 2007/0149987 A1 | 6/2007 | Wellman et al. |
| 2007/0149998 A1 | 6/2007 | Wicks et al. |
| 2007/0149999 A1 | 6/2007 | Szabo et al. |
| 2007/0150002 A1 | 6/2007 | Szabo et al. |
| 2007/0173803 A1 | 7/2007 | Wham et al. |
| 2007/0191712 A1 | 8/2007 | Messerly et al. |
| 2007/0203488 A1 | 8/2007 | Fleming et al. |
| 2007/0213712 A1 | 9/2007 | Buysse et al. |
| 2007/0219549 A1 | 9/2007 | Marshall et al. |
| 2007/0273340 A1 | 11/2007 | Miller et al. |
| 2007/0299439 A1 | 12/2007 | Latterell et al. |
| 2008/0004639 A1 | 1/2008 | Huitema et al. |
| 2008/0009849 A1 | 1/2008 | Goble et al. |
| 2008/0009850 A1 | 1/2008 | Goble et al. |
| 2008/0015615 A1 | 1/2008 | Molitor et al. |
| 2008/0027465 A1 | 1/2008 | Vitali et al. |
| 2008/0027466 A1 | 1/2008 | Vitali et al. |
| 2008/0045942 A1 | 2/2008 | Truckai et al. |
| 2008/0077131 A1 | 3/2008 | Yates et al. |
| 2008/0132888 A1 | 6/2008 | Iida et al. |
| 2008/0132893 A1 | 6/2008 | D'Amelio et al. |
| 2008/0147062 A1 | 6/2008 | Truckai et al. |
| 2008/0188851 A1 | 8/2008 | Truckai et al. |
| 2008/0287948 A1 | 11/2008 | Newton et al. |
| 2008/0294156 A1 | 11/2008 | Newton et al. |
| 2009/0012516 A1 | 1/2009 | Curtis et al. |
| 2009/0043304 A1 | 2/2009 | Tetzlaff et al. |
| 2009/0076506 A1 | 3/2009 | Baker |
| 2009/0093804 A1 | 4/2009 | Newton |
| 2009/0125014 A1* | 5/2009 | Bouthillier ............ A61B 18/04 606/34 |
| 2009/0171353 A1 | 7/2009 | Johnson et al. |
| 2009/0182323 A1 | 7/2009 | Eder et al. |
| 2009/0234355 A1 | 9/2009 | Edwards et al. |
| 2009/0259224 A1 | 10/2009 | Wham et al. |
| 2009/0306660 A1 | 12/2009 | Johnson et al. |
| 2009/0318915 A1 | 12/2009 | Hosier et al. |
| 2010/0042093 A9 | 2/2010 | Wham et al. |
| 2010/0082026 A1 | 4/2010 | Curtis |
| 2010/0114090 A1 | 5/2010 | Hosier |
| 2010/0130971 A1 | 5/2010 | Baily |
| 2011/0319882 A1 | 12/2011 | Kennedy et al. |

(56) References Cited

U.S. PATENT DOCUMENTS

FOREIGN PATENT DOCUMENTS

| JP | 11507857 | A | 7/1999 |
|----|----------|---|--------|
| JP | 2001269353 | A | 10/2001 |
| JP | 2004195192 | A | 7/2004 |
| JP | 2005529639 | A | 10/2005 |
| JP | 2006512959 |   | 4/2006 |
| JP | 2006512959 | A | 4/2006 |
| JP | 2008086776 | A | 4/2008 |
| WO | 2011156310 | A1 | 12/2011 |

OTHER PUBLICATIONS

Horikawa, Yasuhiro, "Japanese Office Action re Application No. 2013-535106", Apr. 21, 2015, p. 10, Published in: JP.

Porter Jr., Gary A, "Office Action re U.S. Appl. No. 13/277,979", Aug. 21, 2014, p. 56, Published in: US.

Porter Jr., Gary A, "Office Action re U.S. Appl. No. 13/277,979", Jul. 1, 2014, p. 10, Published in: US.

Copenheaver, Blaine R., "International Search Report and Written Opinion re Application No. PCT/US2011/039365", Nov. 16, 2011, p. 11, Published in: US.

Copenheaver, Blaine R., "International Search Report and Written Opinion re Application No. PCT/US11/57191", Feb. 14, 2012, p. 13, Published in: US.

Becamel, Philippe, "International Preliminary Report on Patentability re Applcation No. PCT/2011/057191", May 2, 2013, p. 11, Published in: PCT.

Gruber, Stephen S., "Response to Office Action re Application No. 13/277,979", Aug. 11, 2014, p. 9 Published in: US.

Schneider, Laura A., "Response to Office Action re Application No. 13/277,979", Nov. 14, 2014, p. 10, Published in: US.

Yoshida, Masahiro, "Japanese Office Action re Application No. 2015-244121", Nov. 9, 2016, p. 7, Published in: JP.

\* cited by examiner

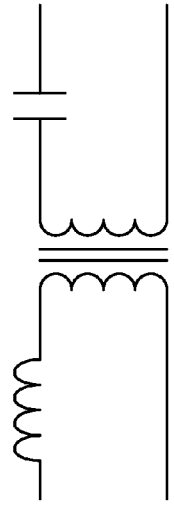
FIG. 3A
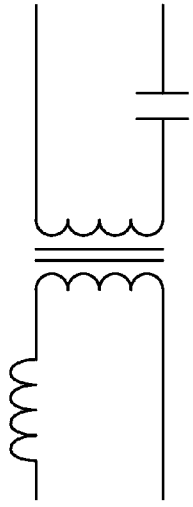
FIG. 3B
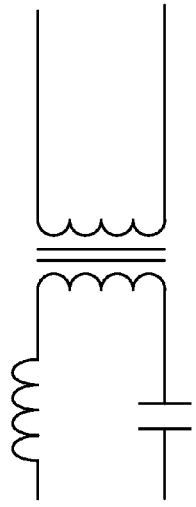
FIG. 3C
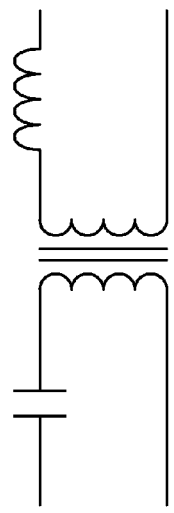
FIG. 3D
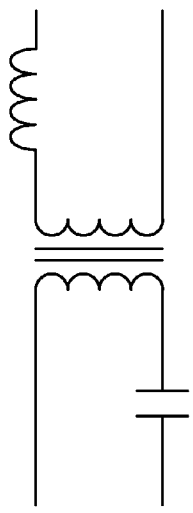
FIG. 3E
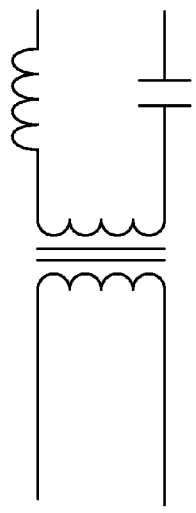
FIG. 3F
← To pulse generator
To electrical output →
FIG. 3

RF GENERATOR SYSTEM FOR SURGICAL VESSEL SEALING

CROSS-REFERENCE TO RELATED APPLICATIONS

This application is a continuation of U.S. application Ser. No. 13/277,979 filed Oct. 20, 2011 and entitled "RF Generator System for Surgical Vessel Sealing," which claims priority to U.S. Provisional Application No. 61/405,761 filed Oct. 22, 2010 and entitled "RF Generator System for Surgical Vessel Sealing," the entire disclosures of which are hereby incorporated by reference for all proper purposes.

FIELD OF THE DISCLOSURE

The present disclosure relates generally to surgical devices. In particular, but not by way of limitation, the present disclosure relates to systems, methods and apparatuses for electrosurgically sealing blood vessels.

BACKGROUND

Electrosurgical tools are used to permanently close vessels in minimally invasive surgical procedures. A combination of pressure and energy initiates collagen melting and tissue fusion. This technology replaces all other hemostasis tools and provides fast and efficient vessel sealing. There are a number of tissue fusion energy devices approved in the market for adult patients, however there is no similar single use device designed for small vessel applications and procedures.

Traditional vessel sealing devices can see sparking and dangerous current spikes when there are short or open situations. Sparking and current spikes result in part from the high currents used as well as energy stored in LC circuits of traditional devices, where the LC circuits are used to generate sinusoidal outputs provided to an electrosurgical instrument. These LC circuits are also often driven at their resonant frequency, which means they offer little impedance when the load impedance drops causing a current spike Traditional vessel sealing devices also use large capacitors and inductors in LC circuits that store substantial energy, thus making it difficult to quickly turn off such devices at the end of an electrosurgical operation.

SUMMARY OF THE DISCLOSURE

Exemplary embodiments of the present invention that are shown in the drawings are summarized below. These and other embodiments are more fully described in the Detailed Description section. It is to be understood, however, that there is no intention to limit the invention to the forms described in this Summary of the Invention or in the Detailed Description. One skilled in the art can recognize that there are numerous modifications, equivalents and alternative constructions that fall within the spirit and scope of the invention as expressed in the claims.

In some aspects, a method of providing power to an electrosurgical instrument includes generating a non-sinusoidal driving voltage having a substantially constant driving frequency; providing the non-sinusoidal driving voltage to a series LC circuit having a resonant frequency of substantially twice the substantially constant driving frequency and configured to present an impedance that limits current spikes and voltage transient spikes during load fluctuations; generating a quasi-sinusoidal current in the series LC circuit from the non-sinusoidal driving voltage; and providing the quasi-sinusoidal current to an electrical output, wherein the electrical output is configured for coupling to an electrical input of a bipolar tissue-sealing surgical instrument.

In some aspects, a power supply for an electrosurgical instrument is provided. The power supply may have a power provider configured to provide a non-sinusoidal voltage at a substantially constant driving frequency and a variable amplitude; a series LC circuit configured to receive the non-sinusoidal voltage and provide a quasi-sinusoidal current, and wherein the resonant frequency of the series LC circuit is substantially twice that of the substantially constant driving frequency; and an electrical output configured to provide the quasi-sinusoidal current to a bipolar tissue-sealing electrosurgical instrument; wherein the electrical output has a maximum voltage of about 75 Volts, and a maximum current of about 1.8 amperes.

BRIEF DESCRIPTION OF THE DRAWINGS

Various objects and advantages and a more complete understanding of the present invention are apparent and more readily appreciated by referring to the following detailed description and to the appended claims when taken in conjunction with the accompanying drawings:

FIGS. 3A-3F illustrate six alternative arrangements of an inductor and capacitor in the LC series circuit.

DETAILED DESCRIPTION

Figure 1:
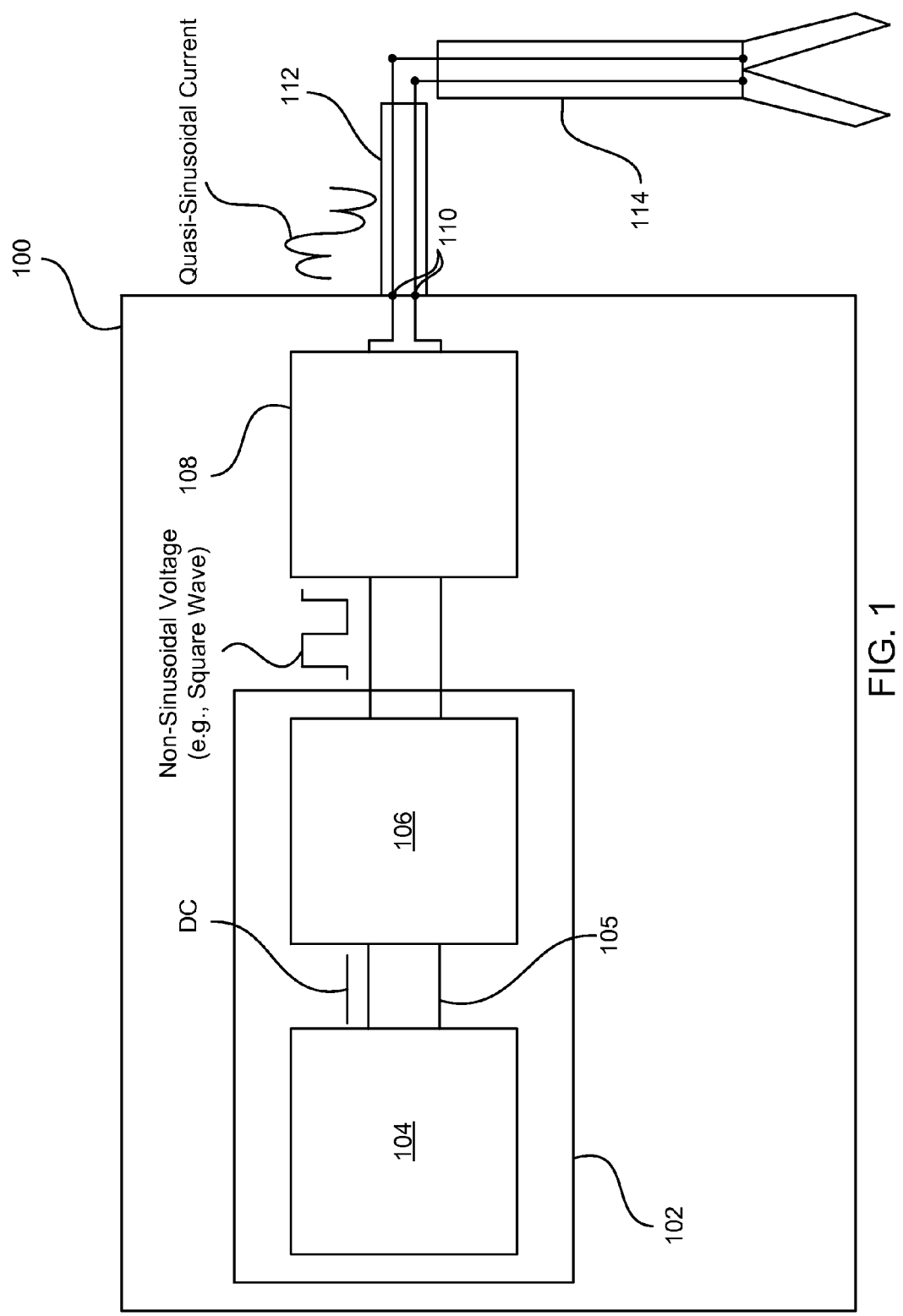
FIG. 1 illustrates a power supply for providing power to an electrosurgical instrument.

FIG. 1 illustrates a power supply for an electrosurgical instrument. The power supply 100 can include a power provider 102, an LC circuit 108, and an electrical output 110, and the power supply 100 can be configured to couple to and provide power to an electrosurgical instrument 114. The power provider 102 can provide a non-sinusoidal voltage (e.g., pulsed DC voltage or a square wave having finite switching time) to the LC circuit 108 (e.g., capacitor and inductor in series). The non-sinusoidal voltage can have a constant, or substantially constant (e.g., plus or minus 50 ppm (0.005%)), drive frequency and a variable amplitude.

The LC circuit 108 can receive the non-sinusoidal voltage and convert the voltage to a quasi-sinusoidal current. The non-sinusoidal voltage, or driving voltage, can operate at substantially half a resonant frequency of the LC circuit 108. Exemplary constant drive frequencies can include the range 225 to 275 KHz, with a plus or minus 50 ppm jitter for any constant drive frequency in that range, where the jitter is inherent to the electronics (e.g., a crystal oscillator).

The constant drive frequency can be initially tuned to one half the LC circuit 108 resonance and parasitic inductances and capacitances, but does not change from one surgical operation to the next (further tuning is possible but not required). In some embodiments, while the resonant frequency of the LC circuit 108 is typically beyond control (assuming fixed capacitors and inductors and neglecting changes in capacitance and inductance for different cables 112), the constant drive frequency of the pulse generator 106 can be tuned to align with the resonance of the LC circuit 108 (e.g., where constant drive frequency is substantially half the resonant frequency). By operating at substantially half the resonant frequency of the LC circuit 108, the LC circuit 108 presents an impedance to current passing through the LC circuit 108 (the quasi-sinusoidal current) as compared to the negligible or substantially negligible impedance that would be seen were the LC circuit 108 driven at or near its resonant frequency.

The quasi-sinusoidal current (e.g., see 404, and 504 in FIGS. 4-5) can be provided to an electrical output 110. The electrical output 110 can be configured for coupling to and providing the quasi-sinusoidal current to an electrosurgical instrument 114 (e.g., a bipolar instrument) via a cable 112. The quasi-sinusoidal current varies depending on load impedance. At lower load impedances (e.g., 6-25Ω), the quasi-sinusoidal current resembles the damped ringing output of an LC circuit with a polarity flip (or 180° phase shift) every cycle. For example, see the current 404 illustrated in FIG. 4. As load impedance increases (e.g., as a vessel is heated during electrosurgical sealing), the quasi-sinusoidal current begins to resemble the driving signal (e.g., pulsed waveform) (e.g., at 75-256Ω). An exemplary quasi-sinusoidal current for such higher impedances can be seen in FIG. 5.

Although a constant drive frequency will be hereinafter referred to, it is to be understood that a substantially constant drive frequency is also intended. The range of constant drive frequencies included is 225-275 KHz and for a targeted constant drive frequency, the electronics may have a frequency stability or jitter of plus or minus 50 ppm. Also, although absolute multiples of frequencies (e.g., twice and three times and four times) will be hereinafter referred to, it will be clear to one of skill in the art that multiples of frequencies can include adjacent frequencies of plus or minus 25 KHz (e.g., 225-275 KHz given a constant frequency of 250 KHz).

In an embodiment, the power provider 102 can include a power source 104 and a pulse generator 106 connected via a DC bus 105. The power source 104 can provide DC power (positive current) at a variable amplitude to the pulse generator 106 via the DC bus 105. The power source 104 can also receive DC power (negative current) at from the pulse generator 106. The pulse generator 106 can receive the variable amplitude DC power and convert it to pulsed voltage having a constant drive frequency and having an amplitude dependent upon the variable amplitude received from the power source 104.

The power provider 102 and/or the included power source 104 can operate in a constant power mode. Constant power means that the voltage and/or current are automatically adjusted to maintain a desired or set power output (to within a margin of error of +/−20%). For instance, as the load impedance increases current decreases, and the voltage output of the power provider 102 increases to offset the current decrease and thus maintain constant power. In another example, as the load impedance falls, the current rises, and the voltage of the power provider 102 decreases to maintain constant power output. Thus, for constant power set to 5 W, constant power may include 4-6 W. For constant power set to 10 W, constant power may include 8-12 W. For constant power set to 15 W, constant power may include 12-18 W. The constant power may include the range 0-20 W, 2-15 W, 5-10 W, 10-14 W, or 5-12 W, to name just a few non-limiting examples. Load impedance is primarily that of the tissue being operated upon by the electrosurgical instrument 214, for instance when grasped between tines of an electrosurgical surgical instrument.

In one embodiment, the power source 104 includes a power converter (e.g., buck-boost converter) capable of upconverting or downconverting current and/or voltage. The power converter can have a controllable amplitude that can be controlled, for instance, via a feedback loop that detects and analyzes one or more of current, voltage, power, and impedance at or near the electrical output 110. The power converter can be of a type configured to both source and absorb current. For instance, one or more capacitors of the power converter can absorb energy if needed and later provide that energy back to the LC circuit 108. The ability to absorb energy enables the LC circuit 108 to periodically (e.g., during a time period of each pulse of the quasi-sinusoidal current) discharge some or all stored energy back into the DC bus 105 and thus accumulate little to no stored energy. This enables less severe sparking and current spiking than traditional power supplies.

Current spikes occur when the load impedance drops quickly and the energy stored in the LC components flows into the load. The energy available for such a current spike is traditionally larger than desired since energy builds up in an LC circuit. Moreover, the current can rise quickly since traditional LC circuits are driven at or near resonance, where the LC circuit has little or negligible impedance. However, here, where energy is discharged during a period of time every cycle of the LC circuit 108, only the energy stored during a single cycle is available for discharge during a short circuit condition, and thus current spikes and sparking are less severe than in the prior art. The severity of these events is also mitigated by the fact that the LC circuit 108 is driven at other than the resonant frequency (e.g., half the resonant frequency). The result is that the LC circuit 108 acts as an impedance to the driving signal and thus limits changes in current as well as absolute current during a current spike.

An additional advantage of not accumulating energy in the LC circuit is that power can be shut off to the electrosurgical device in a shorter amount of time, thus giving surgeons greater control over the surgical endpoint. Additionally, the use of smaller inductors and capacitors in the LC circuit than is done in the art, also shortens the cutoff time.

In comparison, were switching to occur at the resonant frequency of the LC circuit 108, the LC circuit 108 would present 0 or negligible impedance to the current. The result would be more sever current spikes and sparking and the inability to discharge substantially all energy in the LC circuit 108 back to the DC bus 105.

In one embodiment, the pulse generator 106 is an h-bridge. The h-bridge may receive DC power from the power source 104 and output pulsed voltage (e.g., square wave) to the LC circuit 108. The pulsed voltage can be provided at a constant drive frequency that is based on characteristics of the LC circuit 108 (e.g., the resonant frequency of the LC circuit 108). For instance, a substantially constant drive frequency can be set to be substantially one half a resonant frequency of the LC circuit 108. In other words, the drive pulses can alternate polarity ever other cycle of the LC circuit 108 when the LC circuit 108 is driven such that it rings at its resonant frequency. An amplitude of the pulsed power can be dictated by the amplitude of DC power provided by the power source 104. The h-bridge can source and absorb current, which like the power source's 104 ability to source and absorb, enables the LC circuit 108 to discharge energy back to the DC bus 105 during a period of time once per cycle. Such a period of time can include the second half of each pulse of the driving voltage, which preferably correlates to the second half of each period of the quasi-sinusoidal current.

To discharge energy back into the DC bus 105, the driving voltage's polarity can be switched 180° out of phase with a zero crossing of the quasi-sinusoidal current and at a frequency substantially equal to one half the resonant frequency (for low impedance). Operated as such, the LC circuit 108 presents a substantial impedance to current thus presenting an upper limit to current spikes and mitigating the rise in current during a current spike. Also, instead of enabling energy to build and accumulate in the LC circuit 108, stored energy discharges back to the DC bus 105 during one half of each resonant cycle.

For instance, at low load impedance (e.g., 6-26Ω) during the first half of positive and negative voltage pulses from the pulse generator 106, energy passes from the DC bus 105 to the LC circuit 108 and the electrosurgical instrument 114. The DC bus 105 sees positive current and the driving voltage and quasi-sinusoidal current have the same polarity. During the second half of voltage pulses, energy passes from the LC circuit 108 back to the DC bus 105 where it can be stored and then resupplied to the LC circuit 108 and the electrosurgical instrument 114 during the first half of the next voltage pulse. The DC bus 105 sees negative current and the driving voltage and quasi-sinusoidal current have opposite polarity during this time when energy is returned to the DC bus 105.

The LC circuit 108 can include an inductive component (e.g., an inductor) and a capacitive component (e.g., a capacitor) in series. Various configurations of the inductive and capacitive components in the LC circuit 108 can be seen in FIG. 3.

In order to decrease switching losses, pulses can be switched substantially at a minimum current in the LC circuit 108 or when current approaches 0 amperes. This is typically possible at low impedance where current crosses 0 amperes once per resonant cycle of the LC circuit 108 and approaches 0 amperes once per resonant cycle of the LC circuit 108 (see FIG. 4). Switching is preferable, not at the 0 crossing, but at or near to where the quasi-sinusoidal current approaches 0 amperes. At higher impedance, the quasi-sinusoidal current does not approach 0 amperes to the same extent as at low impedance (see FIG. 5), and thus switching losses are more difficult to avoid.

Voltage pulses may have finite switching times, in which case the phasing of the pulsed voltage is selected such that either the beginning, end, or some middle portion of the finite switching time period occurs at the same moment that the quasi-sinusoidal current in the LC circuit 108 approaches 0 amperes (for low impedance).

The LC circuit 108 can be driven at half its resonant frequency, and driven via pulsed or square waves voltages (or some other non-sinusoidal driving waveform). Phasing of the driving voltage pulses may be timed to occur substantially at the moment that the quasi-sinusoidal current in the LC circuit 108 approaches 0 amperes (at low impedance). This unique driving frequency and phasing along with use of a power provider 102 that can source and absorb energy enables the LC circuit 108 to discharge energy back to the power provider 102 during a part of each cycle and thus decrease energy stored in the LC circuit 108. In one embodiment, during pulse transitions, the LC circuit 108 discharges substantially all energy stored therein back to the power provider 102.

Figure 2:
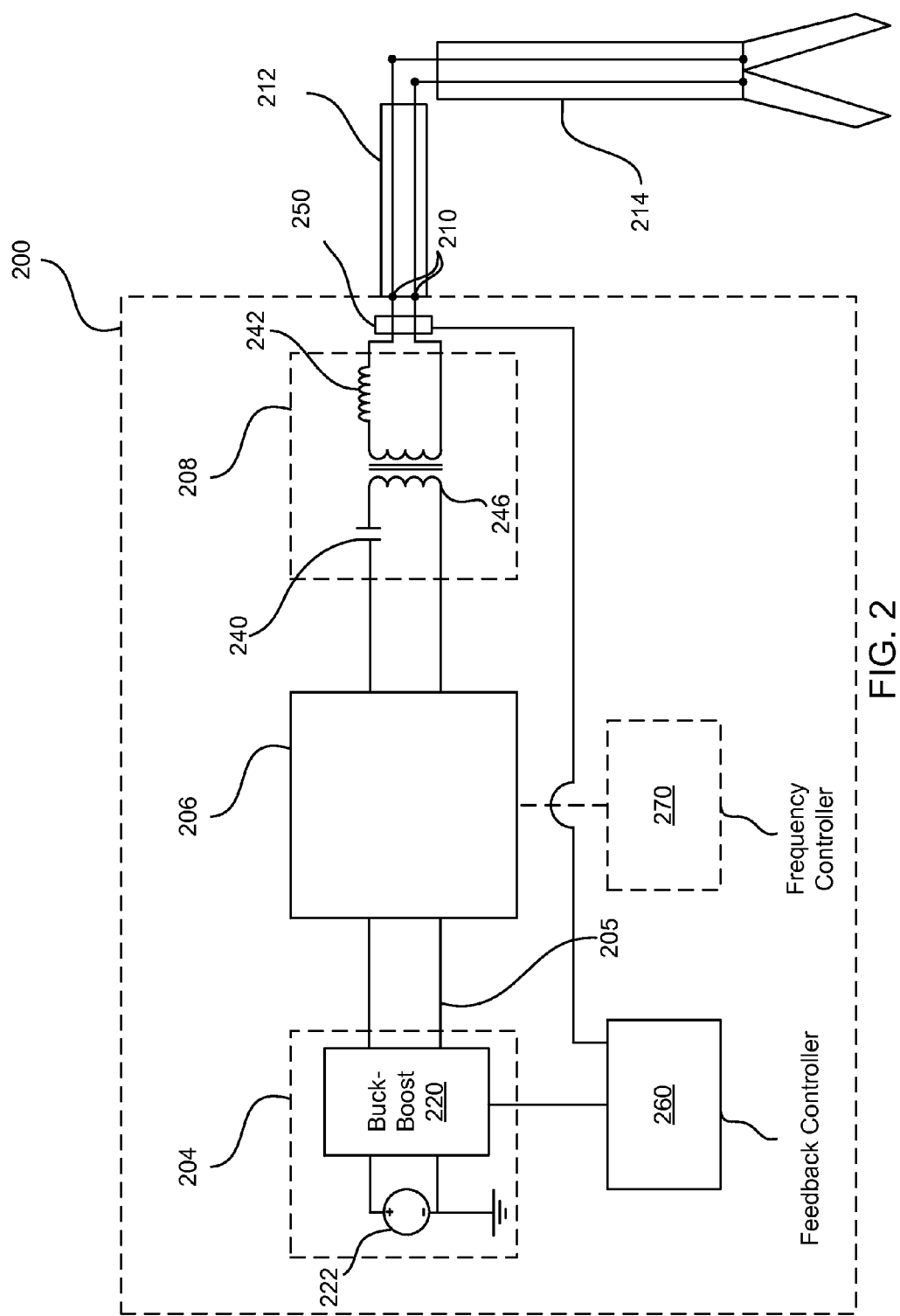
FIG. 2 illustrates another embodiment of a power supply for providing power to an electrosurgical instrument.

FIG. 2 illustrates another embodiment of a power supply for providing power to an electrosurgical instrument. The power supply 200 includes a power source 204, a pulse generator 206 (e.g., an h-bridge), and an LC circuit 208. The power source 204 can include a source 222, and a power converter (e.g., buck-boost converter 220) and be coupled to the pulse generator 206 via a DC bus 205. The LC circuit 218 can include one or more inductive elements (e.g., inductor 242), one or more capacitive elements (e.g., capacitor 240), and a transformer 246. The power supply 200 is also configured to be coupled to a cable 212 via electrical output 210, and the cable 212 can be coupled to an electrosurgical instrument 214 (e.g., a bipolar instrument). The power supply 200 can also include one or more sensors 250 for monitoring various electrical characteristics (e.g., voltage, current, power, impedance) at or near the electrical output 210. The one or more sensors 250 can provide feedback signals to a feedback controller 260 configured to control, or provide instructions for controlling, an amplitude of DC power generated by the power source 204. An optional frequency controller 270 can control a frequency of pulses from the pulse generator 206, and can be controlled via feedback, or can be controlled from a memory (e.g., solid-state memory or disk drive memory) or user input.

The power source 204 can include a power converter such as buck-boost 220 which can upconvert and/or downconvert power from source 222. The buck-boost generates DC power having a variable or controllable amplitude, where the amplitude is controlled by the feedback controller 260. The amplitude of the DC power can depend on various limits such as a current and voltage limit. Current and voltage limits may exist to protect against short and open circuit anomalies. These limits not only provide safety to the surgeon and the patient, but also prevent unexpected electrical phenomena.

In an embodiment, the one or more sensors 250 provide feedback regarding current and voltage at or near the electrical output 210. The feedback controller 260 compares the measured current and/or voltage to current and/or voltage limits or thresholds (e.g., a voltage maximum at 75 volts and a current range of between 1.3 and 1.8 amperes). If the measured current or voltage exceeds a limit or threshold, then the feedback controller 260 can instruct or signal the power source 204 (or the buck-boost 220 of the power source 204) to decrease current and/or voltage.

This decrease can be predetermined (e.g., cutting current by 50%) or can be based on real-time measurements of current and/or voltage. For instance, the current may be decreased until the current or voltage, whichever exceeded a limit, falls below the limit. The rate of decrease may be based on real-time measurements of current, voltage, power, and impedance from the one or more sensors 250. For instance, where current or voltage are observed to exceed the threshold by a certain percentage or are exceeding the threshold at a certain rate, the decrease in voltage may be more severe than if the voltage or current exceeded the threshold or the rate of voltage or current increase were not as great.

There may also be a power limit as defined by a power profile that may be selected based on a desired power profile (e.g., a symmetric or non-symmetric trapezoid) to be applied to tissue during a sealing operation. The one or more sensors 250 can monitor power and provide information regarding the power to the feedback controller 260. The feedback controller 260 can compare the monitored power to a power profile (e.g., stored in a memory) and instruct or signal the power source 204 (or the buck-boost 220 of the power source 204) to decrease power should the monitored power exceed the power profile. The buck-boost 220 may have a tendency to increase power towards the highest current or voltage provided by the source 222, such that the buck-boost 220 provides the highest power possible that does not exceed the thresholds or limits set by the feedback controller 260.

However, it should be noted that the power source 204 and the buck-boost 220 of the power source 204 preferably provide constant power to the DC bus 205. In other words, rather than the power source 204 or buck-boost 220 being a current source (constant current, variable voltage) or a voltage source (constant voltage, variable current), they may have variable current and voltage so as to achieve a constant power output. The advantage of an inherent constant power source is that there is not a critical demand on the feedback circuit to indirectly control power by either controlling voltage or current. This makes the control circuit more reliable and can eliminate transient spikes that may otherwise occur with conventional voltage or current sources.

In one embodiment, the feedback controller 260 controls a switch (e.g., FET) that couples an inductor across output terminals of the source 222. In this state, inductor current rises linearly with time until reaching a current threshold. The current threshold can be based upon feedback from the one or more sensors 250. Once the current reaches the current threshold, the power source 204 provides constant power since any change in impedance results in the power source 204 providing different current and voltage yet maintaining the same power output. The current and voltage of the power source 204 vary automatically as a result of impedance changes, but also due to changes in the constant power output as controlled by the feedback controller 260.

By critical demand on the feedback it is meant that there is a limit to how quickly feedback systems can operate before they become unstable (e.g., faster response leads to greater instability until, at a critical response time, the system becomes unstable).

The power source 204 and the buck-boost 220 are also capable of sourcing and absorbing current (voltage rises when current is absorbed). This characteristic is not common to all power sources, and here provides unique advantage since it aids in preventing buildup of energy in the LC circuit 208 by allowing the LC circuit 208 to return energy to the DC bus 205. In other words, power sources incapable of sourcing and absorbing current may not be capable of achieving the current spike and spark mitigation or rapid cutoff that the power supply 200 is capable of. For instance, the power source 204 may include a buck-boost having a capacitor bank (not illustrated) able to absorb current and then resupply the absorbed current to the LC circuit 208. The absorbed current can be resupplied to the LC circuit 208 in a next resonant cycle of the LC circuit 208.

The pulse generator 206 produces a non-sinusoidal voltage, such as pulsed or square waves. It can also take the form of an h-bridge or any other switched mode power supply, and can produce pulsed or square wave signals. The h-bridge can comprise four field effect transistors (FET) in one embodiment, and the four FETs can diagonally switch on and off to create pulsed power or square waves that alternate the polarity of power being applied to the LC circuit 208.

FETs are chosen that minimize or reduce losses. The pulse generator 206 is capable of sourcing and absorbing current, which, like the power source 204, enables the unique current spike and spark prevention along with rapid cutoff of the power supply 200. The pulse generator 206 produces pulses at a constant drive frequency (e.g., 250 KHz+/−25 KHz or any frequency less than 500 KHz) as dictated by the optional frequency controller 270 and at a variable amplitude where the amplitude is controlled by the DC power provided by the power source 204. In one embodiment, the pulse generator 206 generates a constant driving frequency at 240 KHz with perhaps a +/−5 ppm jitter.

During a surgical operation, the constant driving frequency (frequency of the pulses) is kept constant while amplitude of the voltage pulses can be adjusted via the power source 204. Changes in amplitude of the pulses affect the shape of the quasi-sinusoidal current of the LC circuit 208 (along with load impedance) and thus the average power delivered to the electrosurgical instrument 214. Thus, changes in amplitude of the voltage pulses can be used to track a power profile that is to be applied during a surgical operation (e.g., vessel sealing). The amplitude of DC current and voltage provided by the power source 204 automatically adjusts when the load impedance changes (impedance of the electrosurgical surgical instrument 214) since the buck-boost 220 outputs constant power (for a given set point of the power profile).

Although the switching is described as pulsed or square wave in nature, in practice the 'pulses' can have a trapezoidal shape. In other words, switching time from one pulse to the next is finite. Furthermore, although the circuitry of the power supply enables nearly instantaneous switching (or a pure square wave), this maximum performance of the circuitry may not always be utilized and thus switching may involve a slight ramping up or down in voltage and/or current rather than a discrete jump. Since switching time is finite, the constant drive frequency can be tailored so that the transition between pulses occurs substantially at or near a time when the quasi-sinusoidal current in the LC circuit 208 approaches 0 amperes (at low impedance). In one embodiment, the start of a transition between pulses occurs substantially at the same time as the quasi-sinusoidal current in the LC circuit 208 approaches 0 amperes.

In some embodiments, the optional frequency controller 270 can instruct or signal the pulse generator 206 to provide pulsed voltage to the LC circuit 208 at a constant drive frequency. By constant, it is meant that during a given tissue operation or vessel sealing operation the frequency of pulses delivered to the LC circuit 208 is constant. In other embodiments, the constant driving frequency can be adjusted between operations in order to tune the constant driving frequency to the resonance of the LC circuit 208 (e.g., half the resonant frequency of the LC circuit 208). The resonant frequency of the LC circuit 208 can depend on the inductive (e.g., inductor 242) and capacitive (e.g., 240) elements or components of the LC circuit 208 as well as parasitics (e.g., in a transformer of the LC circuit 208 as well as the cable 212, which is not technically part of the LC circuit 208).

Although not illustrated as having a feedback mechanism, in alternative embodiments, the optional frequency controller 270 can receive feedback signals from the LC circuit 208 indicating electrical characteristics of the LC circuit 208 (e.g., voltage, current, power, load impedance, LC circuit impedance, impedance or reactance of the capacitor 240 or inductor 242, impedance or reactance of parasitic from the transformer 246 and cable 212).

The LC circuit 208 can include one or more capacitive elements (e.g., capacitor 240), one or more inductive elements (e.g., inductor 242), and a transformer 246. The capacitor 240 and inductor 242 can be arranged in series (variations of this arrangement can be seen in FIG. 3). The transformer 246 can also be arranged between the two conductive lines or wires of the LC circuit 208 to provide electrical isolation between the electrosurgical instrument 214 and the rest of the power supply 200. The transformer 246 can have a 1:4 turns ration (primary:secondary) and be wound around a magnetic core using conductive wire having a diameter selected to minimize skin effects (e.g., thin diameter wire). In one embodiment, leakage inductance from the transformer 246 is on the order of no more than 5 µH.

The capacitor 240 can be selected to have a lower capacitance than traditional capacitors used in this capacity, so that less charge is stored in the LC circuit 208. Lower energy being stored in the LC circuit 208 means there is less energy available for discharge into the electrosurgical instrument 214 in the event of a short or open. Lower stored energy means that power can be cutoff faster than in devices using larger inductive and capacitive components. In particular, exemplary capacitance values for the capacitor 240 include, but are not limited to, 0.01-1.0 µF.

The inductor 242 can be a discrete inductor. However, when determining the constant drive frequency of the pulsed voltage provided by the pulse generator 206, the inductance of the LC circuit 208 can be considered to include the value of the discrete inductor 242 as well as parasitic inductances from the transformer 246 and the cable 212, and even the electrosurgical instrument 214. In other words, the resonant frequency of the LC circuit 208 that the pulse generator 206 is tuned to, takes into account parasitic effects and even parasitic effects of the cable 212 and instrument 214 outside of the LC circuit 208.

The capacitor 240 can be discrete, and like the inductance, the capacitance used to determine the LC circuit 208 resonant frequency can depend on the discrete capacitor 240 capacitance as well as parasitic capacitances inside and outside of the LC circuit 208.

In one embodiment, the inductive circuit comprises two or more inductive elements coupled to each other in series or in parallel. The capacitive circuit can comprise two or more capacitive elements coupled to each other in series or in parallel.

The one or more sensors 250 can include a current and voltage sensor. There can also be a power sensor, or the signals from the current and voltage sensors can be used to calculate the power (e.g., voltage times amplitude). There can also be an impedance sensor that measures the load impedance as well as the LC circuit 208 impedance, or these impedances can be calculated based on the current and voltage measured by the current and voltage sensors. Measurements can be taken at or near the output 210. In one embodiment, the one or more sensors 250 can be isolated from the electrosurgical instrument 214, for instance via use of a transformer (not illustrated).

In one embodiment, the inductor 242 and capacitor 240 can be adjusted (e.g., either mechanically or electrically) to change the impedance and reactance of the LC circuit 208 and hence the resonant frequency in order to adapt to changes in the cable 212, electrosurgical instrument 214, and/or the tissue being operated on. For instance, the inductance and capacitance could be electrically altered to account for different electrosurgical instruments 214 being coupled to the power supply 200.

This power supply 200 is advantageous because it inherently produces a desired operation in which at low load impedance the power supply 200 provides high current to the tissue, while at high load impedance (as sealing nears completion) it provides high voltage. In particular, use of a constant power source such as power source 204 inherently produces these electrical characteristics that are not achieved when a current or voltage source are used. For instance, since constant power is being used, the ratio of voltage over current equals impedance. So, as load rises, the ratio of voltage to current increases.

FIGS. 3A-3F illustrate six alternative arrangements of the inductor 242 and capacitor 240 in the LC circuit 208. Each of these configurations fall within this disclosure's definition of an LC circuit (e.g., LC circuit 208) with an inductor and capacitor in series—a series LC circuit. Each of the illustrated configurations could be substituted into FIG. 2 for the LC circuit 208 (FIG. 3A is identical to LC circuit 208 in FIG. 2), where the pulse generator 206 is to the left of FIG. 3 and the electrical output 210 is to the right.

Figure 4:
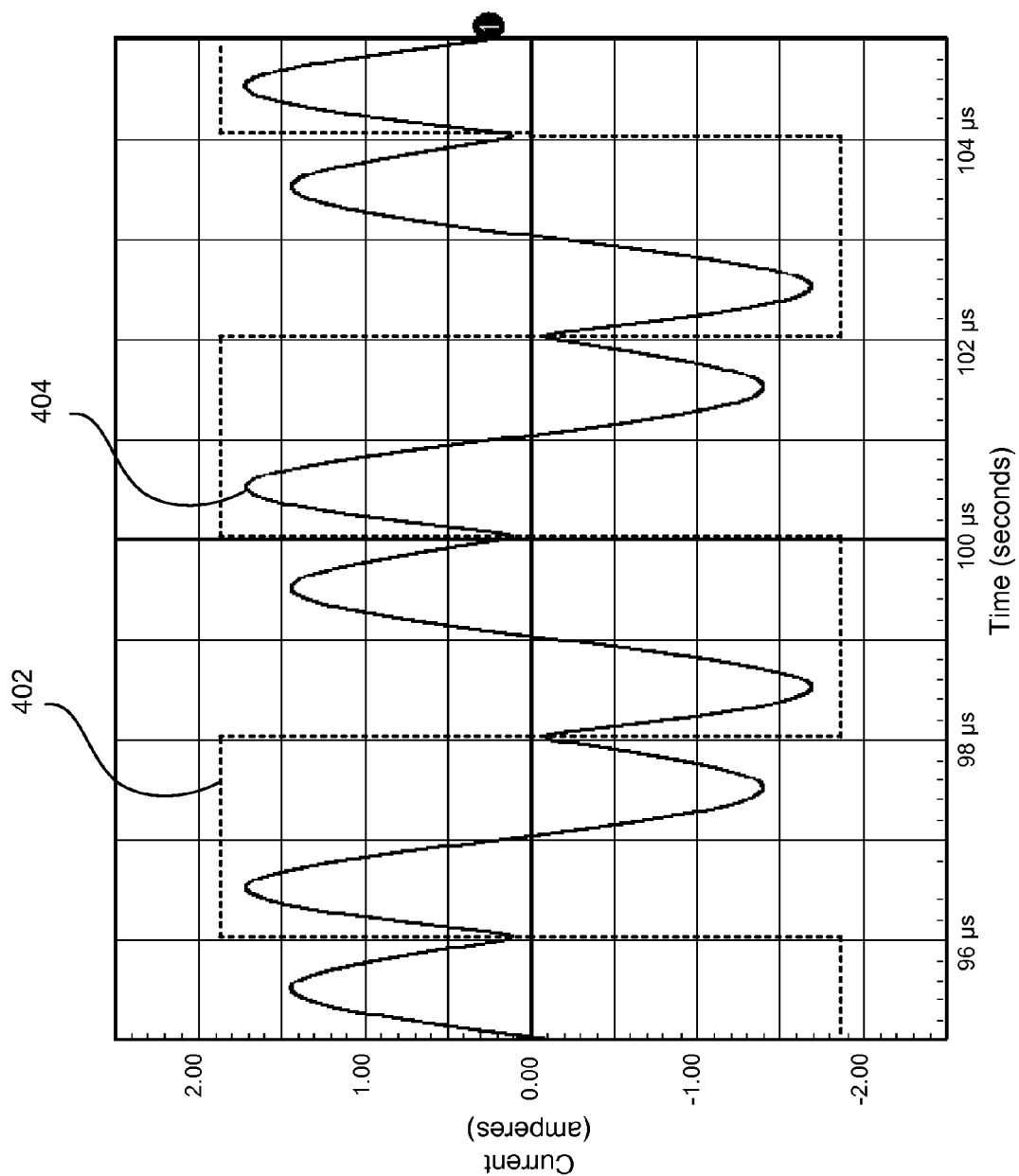
FIG. 4 illustrates current output from one or more of the LC circuits described herein for low load impedances.

FIG. 4 illustrates current in one or more of the LC circuits described herein for low load impedances. Such low load impedances may be seen at the start and early portions of a surgical operation such as vessel sealing. The LC circuit can take the form of those illustrated in FIGS. 1-2 (e.g., 108, 208). Since the LC circuit 108, 208 is a series circuit, the current 404 entering the LC circuit 108, 208, inside the LC circuit 108, 208, and leaving the LC circuit 108, 208 are the same. Similarly, the current 404 between the pulse generator (e.g., 106, 206) and the LC circuit 108, 208 and that provided to the electrosurgical instrument (e.g., 114, 214) is also represented by the current 404 of FIG. 4. Low impedance can include, but is not limited to, a load impedance of 6-25Ω.

A driving voltage 402 from the pulse generator 106, 206 to the LC circuit 108, 208, herein illustrated as a square wave (although other non-sinusoidal waveforms are also envisioned), is switched at half a resonant frequency of the LC circuit 108, 208. The current 404 is in phase with the driving voltage 402 and sees a 180° phase shift once every current 404 cycle, and twice every cycle of the driving voltage 402. The 180° phase shift, or polarity reversal, occurs at approximately 96 µs, 98 µs, 100 µs, 102 µs, and 104 µs.

It should be noted that the values of time and current for the waveforms in FIG. 4 were arbitrarily generated, and thus are not meant to limit the scope of the disclosure. The driving voltage 402 is illustrated with an arbitrary voltage and is not necessarily drawn to scale relative to the current 404.

As seen, the current 404 resembles a dampened sine wave that sees a 180° phase shift or polarity reversal each time the driving voltage 402 from the pulse generator 106, 206 switches. Current 404 crosses 0 amperes near 97 µs, 99 µs, 101 µs, and 103 µs. Current approaches 0 amperes at or near 96 µs, 98 µs, 100 µs, 102 µs, and 104 µs. Although as illustrated, the current 404 does not reach 0 amperes when the driving voltage 402 switches, in other embodiments, the circuitry used is such that the current reaches 0 amperes when the driving voltage 402 switches.

The DC bus (e.g., 105, 205) provides energy to the LC circuit 108, 208 and the electrosurgical instrument 114, 214 whenever the driving voltage 402 and current 404 have the same polarity. For instance, energy is provided to the LC circuit 108, 208 and the electrosurgical instrument 114, 214 during the time periods between: 96-97 µs, 98-99 µs, 100-101 µs, 102-103 µs and 104-105 µs. During these time periods, current in the DC bus 105, 205 is positive. Energy is returned to the DC bus 105, 205 and discharged from the LC circuit 108, 208 whenever the driving voltage 402 and current 404 have opposite polarity. For instance, energy is returned to the DC bus 105, 205 and discharged from the LC circuit 108, 208 during the time periods between: 95-96 µs, 97-98 µs, 99-100 µs, 101-102 µs, 103-104 µs.

Thus, the DC bus 105, 205 provides current and energy during the first half of each driving voltage 402 pulse from the pulse generator 106, 206, and absorbs current and energy during the second half of each driving voltage 402 pulse. As a result, at or near the pulse switching, substantially all energy stored in the LC circuit 108, 208 will have been discharged back to the DC bus 105, 205. Hence, at the start of each driving voltage 402 pulse, the LC circuit 108, 208 is substantially devoid of stored energy. This should be compared to a typical LC circuit, where the inductor and capacitor alternately store a substantial amount of energy throughout an LC circuit cycle.

Figure 5:
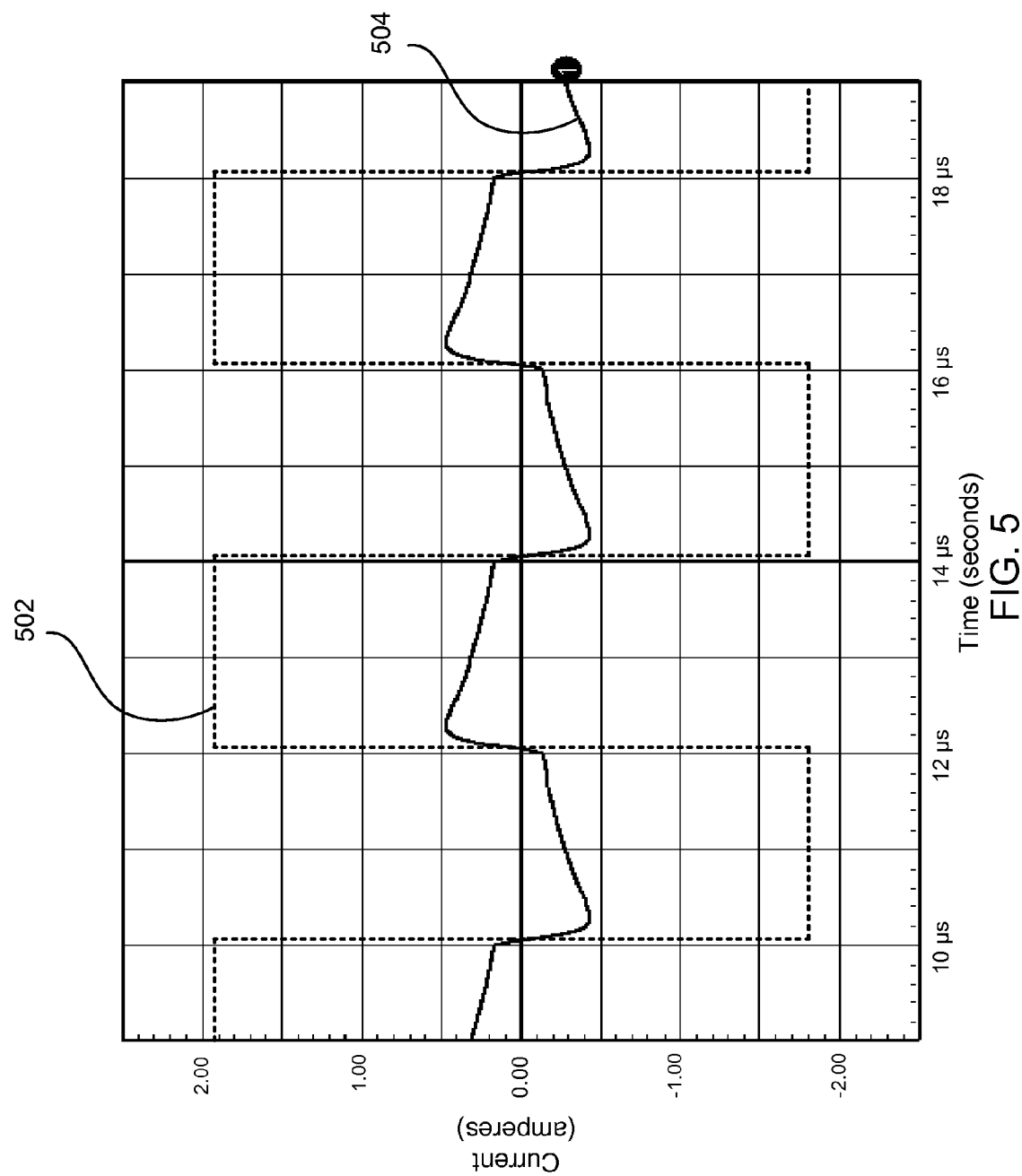
FIG. 5 illustrates current output from one or more of the LC circuits described herein for high load impedances.

FIG. 5 illustrates current output in one or more of the LC circuits described herein for high load impedances. Such high load impedances may be seen near the end or latter portions of a surgical operation such as vessel sealing. The LC circuit can take the form of those illustrated in FIGS. 1-2 (e.g., 108, 208). High impedance can include, but is not limited to, a load impedance of 75-256Ω.

A driving voltage 502 from the pulse generator 106, 206 to the LC circuit 108, 208, herein illustrated as a square wave (although other non-sinusoidal waveforms are also envisioned), is switched at half a resonant frequency of the LC circuit 108, 208. The current 504 is in phase with the driving voltage 502 and sees a 180° phase shift once every current 504 cycle, and twice every cycle of the driving voltage 502. The 180° phase shift, or polarity reversal, occurs at approximately 10 µs, 12 µs, 14 µs, 16 µs, and 18 µs.

It should be noted that the values of time and current for the waveforms in FIG. 5 were arbitrarily generated, and thus are not meant to limit the scope of the disclosure. The driving voltage 502 is illustrated with an arbitrary voltage and is not necessarily drawn to scale relative to the current 504.

Unlike the current 404 for low impedance, at high impedance, ringing in the LC circuit 108, 208 is sufficiently damped that the sinusoidal shape of the current 404 seen in FIG. 4 is not visible in FIG. 5. Rather, the current 504 more closely resembles the pulsed driving voltage 502 that switches at or near 10 µs, 12 µs, 14 µs, 16 µs, and 18 µs. In other words, switching occurs at or near a point where the current 504 crosses 0 amperes. Also, unlike the low impedance situation illustrated in FIG. 4, at higher impedance, energy is only provided from the DC bus 105, 205 to the LC circuit 108, 208 and the electrosurgical instrument 114, 214. As seen, the current 504, and driving voltage 502, are always of the same polarity, and thus energy is not returned to the DC bus 105, 205.

Figure 6:
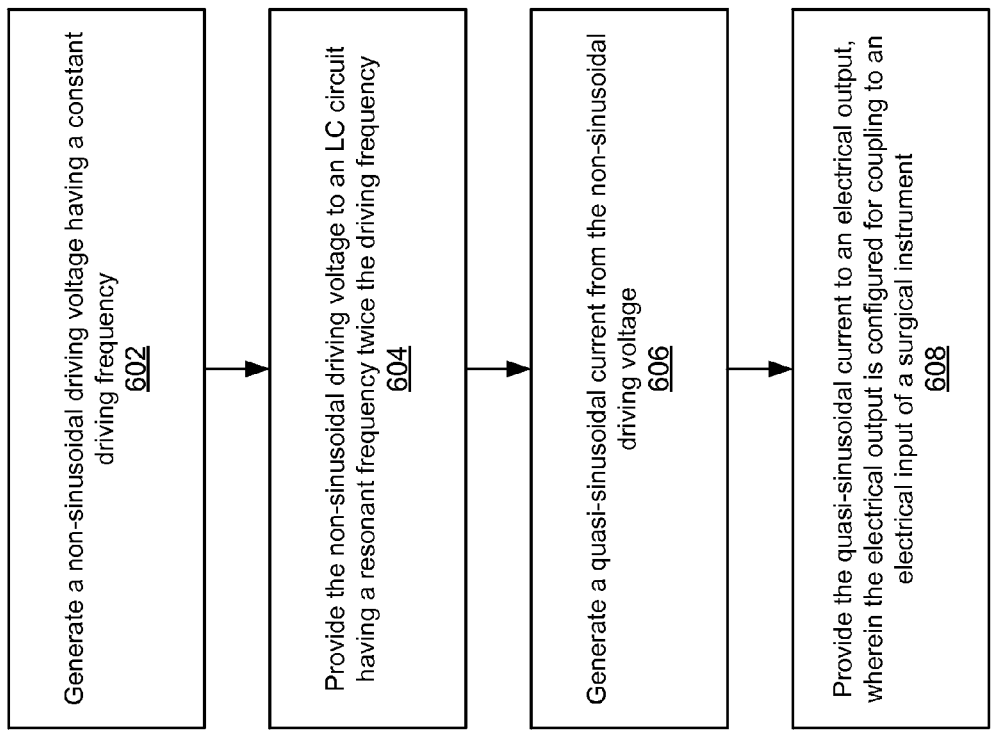
FIG. 6 illustrates a method of providing power to an electrosurgical instrument.

FIG. 6 illustrates a method of providing power to an electrosurgical instrument. The method 600 involves first generating a non-sinusoidal driving voltage having a constant driving frequency in a first generate operation 602. The method 600 further includes providing the non-sinusoidal driving voltage to an LC circuit having a resonant frequency twice the driving frequency in the first provide operation 604. The method also generates a quasi-sinusoidal current from the non-sinusoidal driving voltage in a second generate operation 606. Finally, the method 100 provides the quasi-sinusoidal current to an electrical output in a second provide operation 608. In the second provide operation 608, the electrical output is configured for coupling to an electrical input of a surgical instrument.

The generate operation 602 can be carried out, for instance, via a power provider 102 (see FIG. 1), or the combination of a power source 204 and a pulse generator 206 (see FIG. 2). The non-sinusoidal driving voltage can be a pulsed waveform such as a square wave, where the waveform can be shaped via an h-bridge of the pulse generator 206 that receives DC power from a power source 204 that can include a buck-boost converter 220. The constant driving frequency can be controlled via a controller such as the optional frequency controller 270.

The first provide operation 604 can provide the non-sinusoidal driving voltage to an LC circuit (e.g., LC circuit 208). The non-sinusoidal driving voltage can be tuned, prior to a surgical operation (e.g., during manufacturing, or during periodic technician tune-ups), to a frequency equivalent to one half of a resonant frequency of the LC circuit (e.g., one half the resonant frequency). By driving the LC circuit at half its resonant frequency, the LC circuit presents an impedance to the driving signal and current passing through the LC circuit that mitigates current spikes and sparking. Driving the LC circuit at half its resonant frequency also enables the LC circuit to discharge energy stored therein every resonant cycle back to the power source (e.g., power source 204), thus leaving less stored energy available for current spikes and sparking. The lower level of stored energy also enables faster cutoff times when a surgical operation ends. Also, current spikes and sparking are less severe than in the art since the LC circuit impedance limits current changes and creates an upper limit on current.

The resonant frequency can be determined based on capacitance and inductance of discrete capacitive and inductive devices in the LC circuit (e.g., of capacitor 240 and inductor 242) as well on parasitic capacitance and inductance (e.g., of transformer 246 and cable 212).

The second generate operation 606 generates a quasi-sinusoidal current using a circuit such as LC circuit 208. For instance, in the LC circuit 208, a pulsed voltage may be converted to the quasi-sinusoidal currents illustrated in FIGS. 4-5. The quasi-sinusoidal current can be provided to an electrical output such as output 110, 210 in the second provide operation 608. The electrical output can be configured for coupling to a cable (e.g., cable 212) and the cable can couple to a surgical instrument (e.g., surgical instrument 214).

Figure 7:
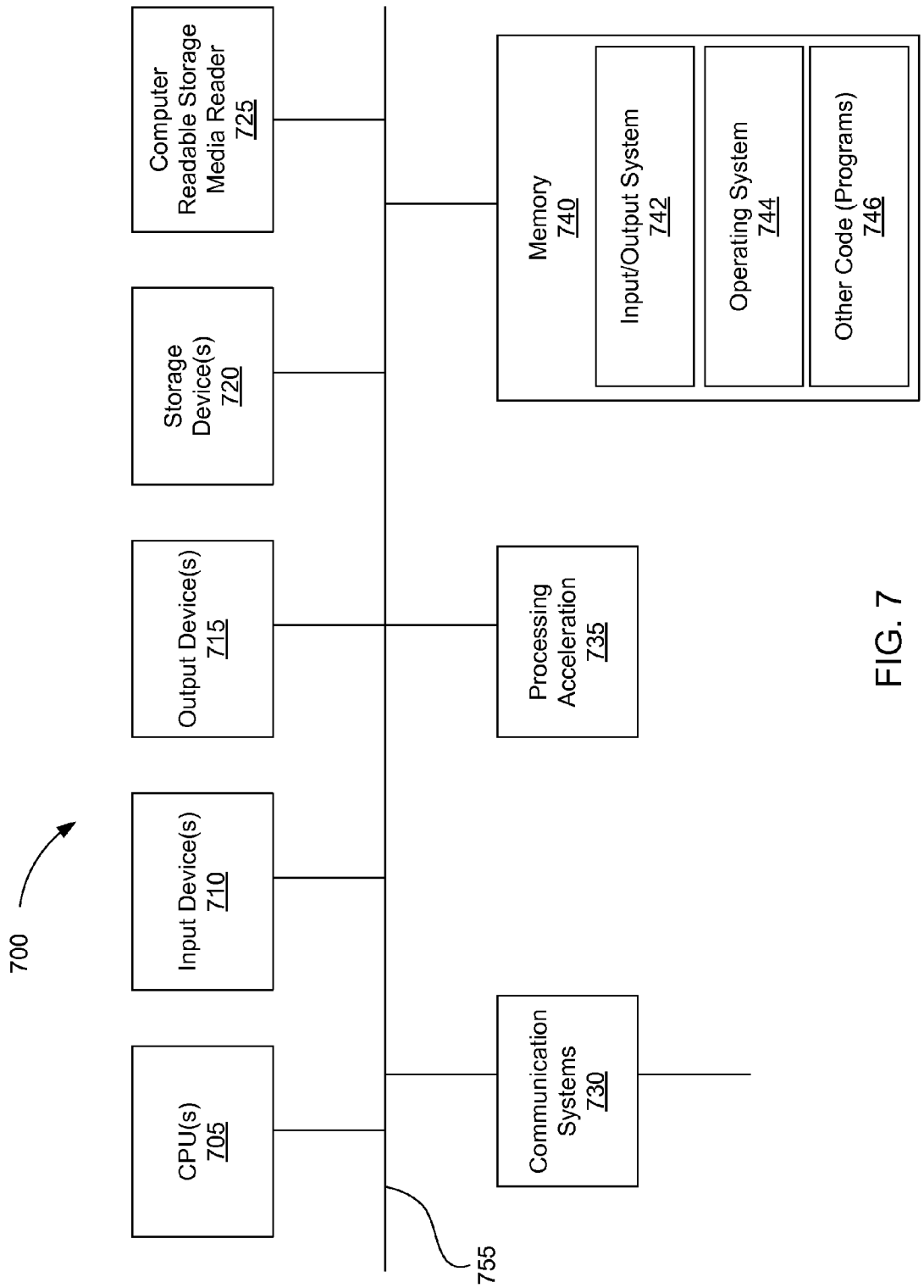
FIG. 7 shows a diagrammatic representation of one embodiment of a machine in the exemplary form of a computer system within which a set of instructions for causing a device to perform any one or more of the aspects and/or methodologies of the present disclosure to be executed.

The systems and methods described herein can be implemented in a machine such as a computer system in addition to the specific physical devices described herein. FIG. 7 shows a diagrammatic representation of one embodiment of a machine in the exemplary form of a computer system 700 within which a set of instructions for causing a device to perform any one or more of the aspects and/or methodologies of the present disclosure to be executed. Computer system 700 includes a processor 705 (or CPU) and a memory 740 that communicate with each other, and with other components, via a bus 755. For instance, the feedback controller 260 and/or the optional frequency controller 270 can include a processor such as processor 705. Bus 755 may include any of several types of bus structures including, but not limited to, a memory bus, a memory controller, a peripheral bus, a local bus, and any combinations thereof, using any of a variety of bus architectures.

Memory 740 may include various components (e.g., machine readable media) including, but not limited to, a random access memory component (e.g., a static RAM "SRAM", a dynamic RAM "DRAM", EEPROM, etc.), a read only component, and any combinations thereof. In one example, a basic input/output system 742 (BIOS), including basic routines that help to transfer information between elements within computer system 700, such as during start-up, may be stored in memory 740. Memory 740 may also include (e.g., stored on one or more machine-readable media) instructions or code (e.g., software) 746 embodying any one or more of the aspects and/or methodologies of the present disclosure. In another example, memory 740 may further include any number of program modules including, but not limited to, an operating system 744, one or more application programs 746, other program modules 746, program data 746, and any combinations thereof. For instance, the memory 740 can store data describing a desired power profile to be used by a controller, such as feedback controller 260 (see FIG. 2) to control a power source, such as power source 204. The memory 740 may also include data describing settings for the constant drive frequency and variable amplitude as a function of the type of electrosurgical instrument 214 being used with the power supply 200. The memory 740 may also contain voltage, current, and power thresholds that the feedback controller 260 can use to mitigate voltage and current spikes as well as to help the power track a power profile.

Computer system 700 may also include a storage device 720. Examples of a storage device (e.g., storage device 720) include, but are not limited to, a hard disk drive for reading from and/or writing to a hard disk, a magnetic disk drive for reading from and/or writing to a removable magnetic disk, an optical disk drive for reading from and/or writing to an optical media (e.g., a CD, a DVD, etc.), a solid-state memory device, and any combinations thereof. Storage device 720 may be connected to bus 755 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 720 may be removably interfaced with computer system 700 (e.g., via an external port connector (not shown)). For instance, the system 700 may include a computer readable storage media reader 725 and an associated machine-readable medium (not illustrated) may provide nonvolatile and/or volatile storage of machine-readable instructions, data structures, program modules, and/or other data for computer system 700. In one example, software 746 may reside, completely or partially, within the machine-readable medium and be accessed via the computer readable storage media reader 725. In another example, software 746 may reside, completely or partially, within processor 705.

Computer system 700 may also include an input device 710. In one example, a user of computer system 700 may enter commands and/or other information into computer system 700 via input device 710. Examples of an input device 710 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), touch screen, and any combinations thereof. Input device 710 may be interfaced to bus 755 via any of a variety of interfaces (not shown) including, but not limited to, a serial interface, a parallel interface, a game port, a USB interface, a FIREWIRE interface, a direct interface to bus 755, and any combinations thereof. For instance, a user can enter the constant drive frequency into the optional frequency controller 270 via the input device 740.

A user may also input commands and/or other information to computer system 700 via computer readable storage media reader 725 (e.g., a removable disk drive, a flash drive, etc.) and/or a communication system 730. The communication system 730 may be utilized for connecting computer system 700 to one or more of a variety of networks and one or more remote devices. Examples of a communication system include, but are not limited to, a network interface card, a modem, and any combination thereof. Examples of a network or network segment include, but are not limited to, a wide area network (e.g., the Internet, an enterprise network), a local area network (e.g., a network associated with an office, a building, a campus or other relatively small geographic space), a telephone network, a direct connection between two computing devices, and any combinations thereof. A network may employ a wired and/or a wireless mode of communication. In general, any network topology may be used. Information (e.g., data, software 746, etc.) may be communicated to and/or from computer system 700 via communication system 730.

Computer system 700 may further include output devices (e.g., a video display adapter) for communicating with peripherals such as a display device. Examples of a display device include, but are not limited to, a liquid crystal display (LCD), a cathode ray tube (CRT), a plasma display, and any combinations thereof. In addition to a display device, the computer system 700 may include one or more other output devices 715 including, but not limited to, an audio speaker, a printer, and any combinations thereof. Such output devices 715 may be connected to bus 755 via a peripheral interface. Examples of a peripheral interface include, but are not limited to, a serial port, a USB connection, a FIREWIRE connection, a parallel connection, and any combinations thereof. In one example an audio device may provide audio related to data of computer system 700 (e.g., data representing an indicator related to pollution impact and/or pollution offset attributable to a consumer).

A digitizer (not shown) and an accompanying stylus, if needed, may be included in order to digitally capture freehand input. A pen digitizer may be separately configured or coextensive with a display area of display device. Accordingly, a digitizer may be integrated with display device, or may exist as a separate device overlaying or otherwise appended to display device.

In conclusion, the present invention provides, among other things, a method, system, and apparatus for driving an LC circuit at half its resonant frequency and providing a quasi-sinusoidal current from the LC circuit for use by an electrosurgical instrument. The quasi-sinusoidal current has less severe current spikes and sparking than those seen in the prior art. Those skilled in the art can readily recognize that numerous variations and substitutions may be made in the invention, its use, and its configuration to achieve substantially the same results as achieved by the embodiments described herein. Accordingly, there is no intention to limit the invention to the disclosed exemplary forms. Many variations, modifications, and alternative constructions fall within the scope and spirit of the disclosed invention.

What is claimed is:

1. A method of providing power to an electrosurgical instrument comprising:
   generating a non-sinusoidal driving voltage having a substantially constant driving frequency;
   providing the non-sinusoidal driving voltage to a series LC circuit having a resonant frequency of substantially twice the substantially constant driving frequency and configured to present an impedance that limits current spikes and voltage transient spikes during load fluctuations;

at least one of upconverting or downconverting the non-sinusoidal driving voltage;

generating a constant power having a quasi-sinusoidal current in the series LC circuit from the non-sinusoidal driving voltage; and providing the constant power having the quasi-sinusoidal current to an electrical output, wherein the electrical output has a maximum threshold voltage of about 75 Volts, and wherein the electrical output is configured for coupling to an electrical input of a bipolar tissue-sealing surgical instrument.

2. The method of claim 1, wherein the non-sinusoidal driving voltage is a pulsed waveform.

3. The method of claim 2, wherein the non-sinusoidal driving voltage is a square wave.

4. The method of claim 3, wherein the non-sinusoidal driving voltage is generated by a power provider, the method further comprising discharging substantially all energy stored in the series LC circuit by returning the energy to the power provider during a time period that occurs once per resonant cycle of the series LC circuit.

5. The method of claim 4, further comprising discharging into the power provider substantially all energy stored in the series LC circuit during the time period that occurs once per resonant cycle of the series LC circuit so that the quasi-sinusoidal current in the series LC circuit approaches 0 amperes during switching of the square wave.

6. The method of claim 5, wherein the time period is a second half of each half cycle of the square wave.

7. The method of claim 1, wherein the non-sinusoidal driving voltage is generated by a power provider, and the method further comprising periodically discharging the series LC circuit by returning energy to the power provider.

8. The method of claim 1, wherein the generating is performed via a constant power mode of a power provider to maintain a desired power.

9. The method of claim 1, further comprising absorbing in a power provider substantially all energy stored in the series LC circuit during a period of time once per resonant cycle of the series LC circuit and resupplying the substantially all energy back to the series LC circuit.

10. A power supply for an electrosurgical instrument comprising:

a power provider configured to provide a non-sinusoidal voltage at a substantially constant driving frequency and a variable amplitude;

a series LC circuit configured to receive the non-sinusoidal voltage and provide a constant power having a quasi-sinusoidal current from the non-sinusoidal driving voltage, wherein the resonant frequency of the series LC circuit is substantially twice that of the substantially constant driving frequency, and wherein the series LC circuit is configured to present an impedance that limits current spikes and voltage transient spikes during load fluctuations;

a buck-boost converter configured to at least one of upconvert or downconvert the non-sinusoidal driving voltage; and an electrical output configured to provide the quasi-sinusoidal current to a bipolar tissue-sealing electrosurgical instrument; wherein the electrical output has a constant power having a maximum voltage of about 75 Volts, and a maximum quasi-sinusoidal current of about 1.8 amperes, wherein the electrical output is configured for coupling to an electrical input of a bipolar tissue-sealing surgical instrument.

11. The power supply of claim 10, wherein the power supply includes a power provider in series with a pulse generator.

12. The power supply of claim 11, wherein the buck-boost converter is configured to provide and receive DC current to and from the pulse generator, where the amplitude of the DC current controls the variable amplitude of the power provider.

13. The power supply of claim 12, wherein the pulse generator includes an h-bridge for receiving and providing the DC current from and to the buck-boost converter via a DC bus, and providing pulsed voltage to the series LC circuit at the substantially constant driving frequency.

14. The power supply of claim 13, wherein the pulsed voltage is a square wave.

15. The power supply of claim 14, wherein:

energy passes from the DC bus to the h-bridge and to the series LC circuit during a first half of each pulse of the square wave; and energy passes from the series LC circuit to the h-bridge to the DC bus during a second half of each pulse of the square wave.

16. The power supply of claim 15, wherein the series LC circuit discharges substantially all energy stored therein to the DC bus during the second half of each pulse of the square wave.

17. The power supply of claim 10, wherein the power provider operates in a constant power mode to maintain a desired power.

18. The power supply of claim 10, wherein the non-sinusoidal voltage is a pulsed voltage.

19. The power supply of claim 10, wherein the power provider absorbs substantially all energy stored in the series LC circuit during a period of time once per resonant cycle of the series LC circuit and resupplies the substantially all energy back to the series LC circuit.

* * * * *